United States Patent [19]
Borghi

[11] Patent Number: 5,482,037
[45] Date of Patent: Jan. 9, 1996

[54] ELECTRODE CATHETER FOR MAPPING AND OPERATING ON CARDIAC CAVITIES

[75] Inventor: Enzo Borghi, Budrio, Italy

[73] Assignee: X-Trode S.R.l., Bologna, Italy

[21] Appl. No.: 180,683

[22] Filed: Jan. 13, 1994

[30] Foreign Application Priority Data

Jan. 18, 1993 [IT] Italy ................................ B093A0008

[51] Int. Cl.⁶ .......................... A61B 5/042; A61B 17/36
[52] U.S. Cl. .................. 128/642; 128/657; 128/658; 128/696; 128/700; 607/122; 607/125; 606/124
[58] Field of Search .................................. 128/642, 657, 128/658, 696, 700, 635, 634; 606/124, 32, 47, 33, 41; 607/122, 125

[56] References Cited

U.S. PATENT DOCUMENTS

| | | |
|---|---|---|
| 452,220 | 5/1891 | Gunning ................................ 607/122 |
| 4,660,571 | 4/1987 | Hess et al. . |
| 4,757,827 | 7/1988 | Buchbinder et al. . |
| 4,848,352 | 7/1989 | Pohndorf et al. . |
| 4,969,463 | 11/1990 | Dahl et al. . |
| 5,313,943 | 5/1994 | Houser et al. ........................ 607/122 |

FOREIGN PATENT DOCUMENTS

| | | |
|---|---|---|
| 92301264 | 2/1992 | European Pat. Off. . |
| 2800362 | 7/1978 | Germany . |

*Primary Examiner*—Angela D. Sykes
*Assistant Examiner*—Stephen Huang
*Attorney, Agent, or Firm*—Fay, Sharpe, Beall, Fagan, Minnich & McKee

[57] ABSTRACT

An electrode catheter for intravenous insertion into a cavity of the heart comprises a tubular sheath accommodating a first spiral wound wire of conductive biocompatible material, which affords an insulated operative portion exposed from the sheath and capped distally by a domed ring, and a mapping electrode of conductive biocompatible material for sensing the electrical activity in the cardiac muscle, which is carried coaxially by the first spiral wound wire and capable of movement along the operative portion transmitted by means of a second spiral wound wire extending coaxially through the first and connected to an external control handset. The operative portion of the first wire is arched by means of a tension wire designed to establish a restraint between the domed ring and the distal end of the sheath, of which the length can be increased or reduced to alter the loop of the arched profile as expedient for the shape of the cavity explored.

31 Claims, 4 Drawing Sheets

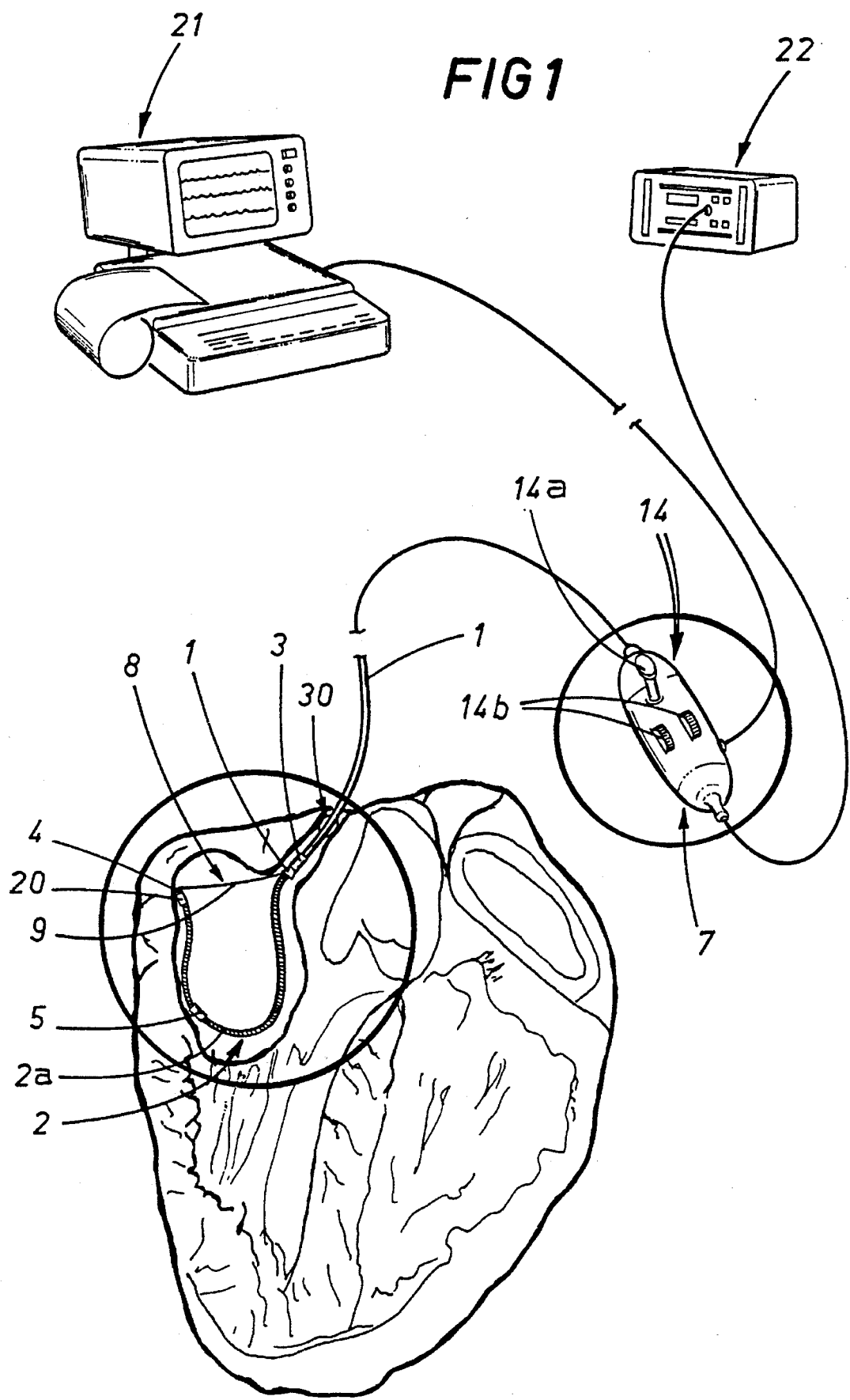

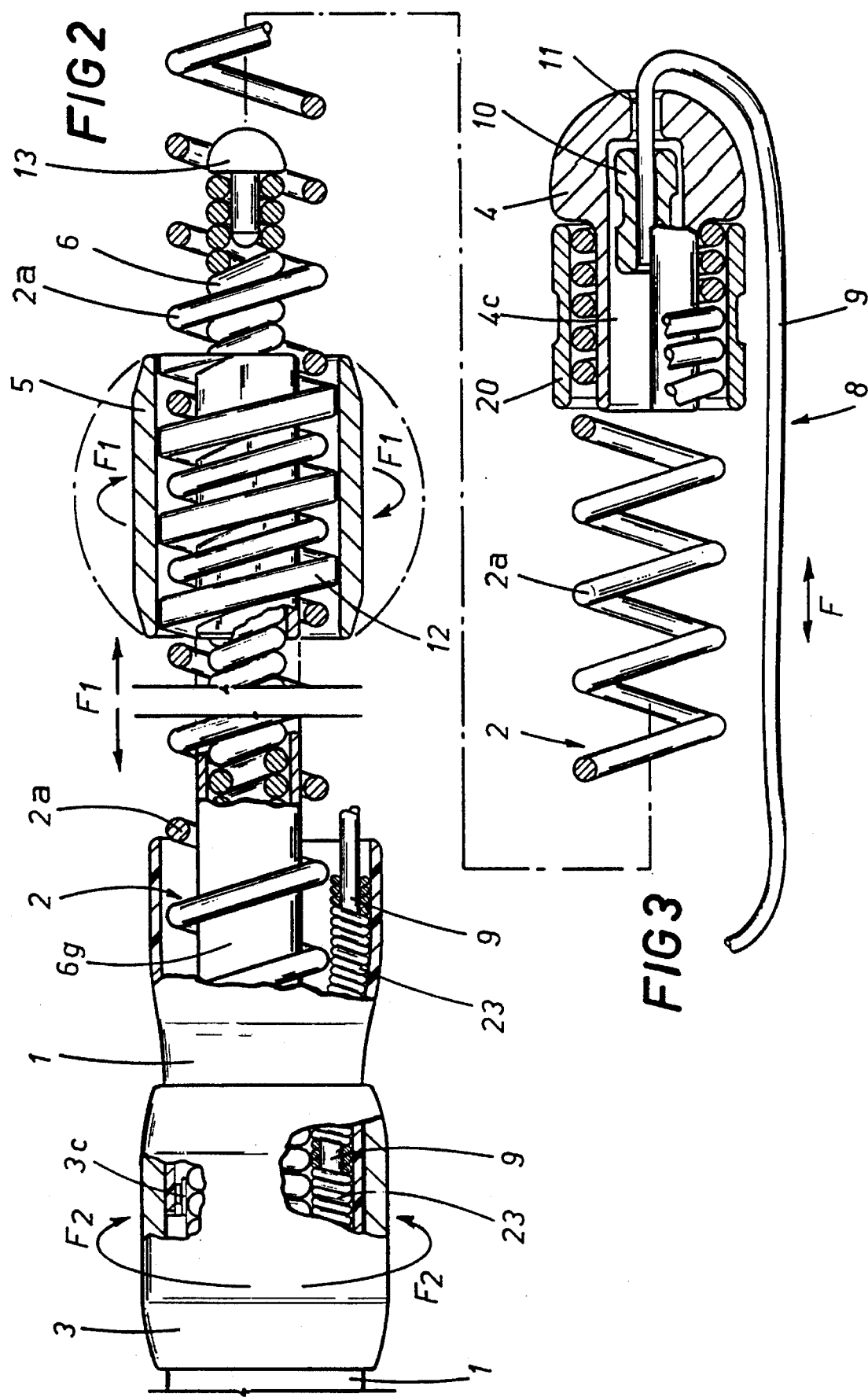

5,482,037

ELECTRODE CATHETER FOR MAPPING AND OPERATING ON CARDIAC CAVITIES

BACKGROUND OF THE INVENTION

The present invention relates to an electrode catheter by means of which to map and if necessary perform an ablation internally of a cardiac cavity, in particular the right and left atria, the mitral valve and the ventricle.

Among the aims currently being pursued in medical and surgical technology, assisted not least by an increasingly widespread miniaturization and greater precision of the equipment available, there is a move toward the creation of a family of instruments which can be used, on the one hand, to monitor all such electrical activities of the cardiac muscle as will tend to widen the scope for the prevention of heart trouble, and on the other, simultaneously and where necessary, to perform a surgical operation. Whilst the measurement of electrical activity in the cardiac muscle is central to a full exploration of the cardiac cavities, the process of effecting the measurement is made difficult by the particular anatomy of the organ; the internal characteristics of the heart do not respond to a standard pattern, in effect, but vary from patient to patient.

As regards the treatment of heart diseases likely to generate situations of serious trouble, to the point of triggering fibrillation, the following options are available:

open heart surgery, performed to remove the zone affected by the trouble: an operation accompanied by risks and consequences well known to a person skilled in the art;

installation of a defibrillator device, which will detect the trouble at the moment of onset and counteract the effect by producing a high voltage electrical discharge through a catheter implanted permanently in the patient: a solution involving high risk to the patient (insofar as the discharge can occur at any moment and without warning) and considerable cost:

non-invasive sensing of the trouble zone by means of a probe, with immediate ablation of the affected muscle fibres: a more recently introduced technique which involves the least risk and disturbance for the patient.

At the time of filing the present application, the prior art embraces few instruments of diagnosis or surgery that can be utilized non-invasively in the manner referred to above, or at least to carry out an accurate measurement and a swift verification of the electric activity in the cardiac muscle. One such instrument consists in a unipolar or multipole electrode catheter insertable into the myocardium through a vein, of which the inserted end affords a sensor (or indeed a plurality of sensors in the case of a multipole type) connected electrically to external monitoring means, which can be maneuvered around internally of the cardiac zone in question. The catheter consists for practical purposes in a pair of parallel control wires united at one end by the terminal sensor and linked at the remaining or non-operative end to a control device functioning in the manner of a tiller, which when rotated one way or the other will impinge on a corresponding wire, causing the end of the catheter that carries the sensor or sensors to assume an arched profile; the arched portion can then be revolved through a plurality of positions in space by rotating the catheter about its own axis.

In this way, the surgeon can effectively "copy" the profile of the explored cardiac zone by sampling the electrical activity of the muscle discretely, with the aid of auxiliary computerized monitoring equipment which is programmed to make allowance for the dimensions of the electrode catheter, and in particular the distance of the operative portion from the point at which the catheter enters the cardiac cavity (referred to generally as the "zero" reference), and to calculate and map the copied profile by interpolation of the discontinuously monitored input data.

In the event that the exploration should reveal an irregular electrical activity in certain cardiac tissues, the selfsame device can be used by the surgeon to carry out an ablation in loco, that is, to burn away a small bundle of muscle fibres and thus eliminate the site of the irregular activity, by means of the terminal sensor utilized previously in the mapping operation; this would be effected with the aid, for example, of a radio frequency device.

The mapping device briefly outlined above betrays considerable drawbacks, however: the configuration of the catheter and the structuring of the wires and the relative control system combine to limit the radius of curvature available to the operative portion and thus allow no more than an approximate scanning and measurement of the cardiac cavities; also, the operations of calibrating and resetting the instruments are lengthy (even for very small dimensions) not least by reason of the fact that the reset (i.e. initial recognition of the "zero" reference) must be effected with a separate probe catheter which, once the position internally of the cardiac cavity has been located, will be removed to allow space for insertion of the mapping catheter, which in its turn must be positioned initially in relation to the zero reference in order to ensure that the zone is mapped correctly. Such a procedure obviously dictates a marked extension of the times required simply to perform the various steps, and this could be damaging to the patient ultimately, especially in cases where there may be the need to perform an ablation at sites registering irregular electrical activity.

In a further solution, disclosed in EP 499 491, the operative portion of the catheter incorporates a plurality of sensing poles or electrodes uniformly distributed along a probe capable of expanding axially in such a way as to allow of altering the distance between the single electrodes, from which corresponding signals are returned to an external controller; the multipole version of this device is somewhat complex, and in any event the catheter can not easily be adapted and matched to the different shapes of the cavities explored. As a result, there are difficulties in effecting the measurement part of the mapping operation, which remains lengthy and imprecise.

Accordingly, the object of the present invention is to overcome the drawbacks mentioned previously, by providing a cardiac mapping and ablation catheter of constructionally simple architecture, affording a wide range of configurations and thus adaptable to any cardiac cavity, while ensuring precision and completeness in every movement and in control over the configurations selected; such a catheter will allow a total and continuous scan of the zones of electrical activity and guarantee especially short operating times whether in monitoring or performing an ablation of cardiac tissue, and can be offered in a disposable format at relatively low cost.

SUMMARY of the INVENTION

The stated object is fully realized in an electrode catheter of the type insertable intravenously into a cavity of the heart, consisting essentially in a tubular outer sheath and at least one spiral wound wire of conductive biocompatible material, encased by the sheath, which in the case of the catheter disclosed is extended beyond the sheath to afford an exposed and insulated operative portion. The catheter disclosed further comprises a first ring in a fixed position near to the distal end of the sheath, a second ring secured to and capping the distal extremity of the operative portion, and a medial third ring of conductive biocompatible material, performing the function of a sensor for the measurement of electrical cardiac activity, which is associated coaxially with and capable of translatory movement along the operative portion through the agency of a further spiral wound wire, disposed coaxially to the first wire, permanently associated with the sensor at one end and connected to externally operated control means at the other. Also forming part of the catheter are means by which to alter the configuration of the operative portion of the first wire, consisting in a flexible tension wire linking the second ring and the distal extremity of the sheath, which can be extended or retracted axially to increase or reduce the length of the link, according to the morphology of the cavity, in such a manner that the operative portion is brought into contact with the entire surface of the cavity by rotating the catheter through 360°.

BRIEF DESCRIPTION OF THE DRAWINGS

The invention will now be described in detail, by way of example, with the aid of the accompanying drawings in which:

FIG. 1 illustrates the mapping electrode catheter according to the invention in a perspective view, connected to monitoring instruments, with certain details enlarged;

FIG. 2 and FIG. 3 are enlarged side elevations of the operative portion of the catheter according to the invention, in which certain parts are seen in section and others cut away;

DESCRIPTION OF THE PREFERRED EMBODIMENTS

Figure 4:
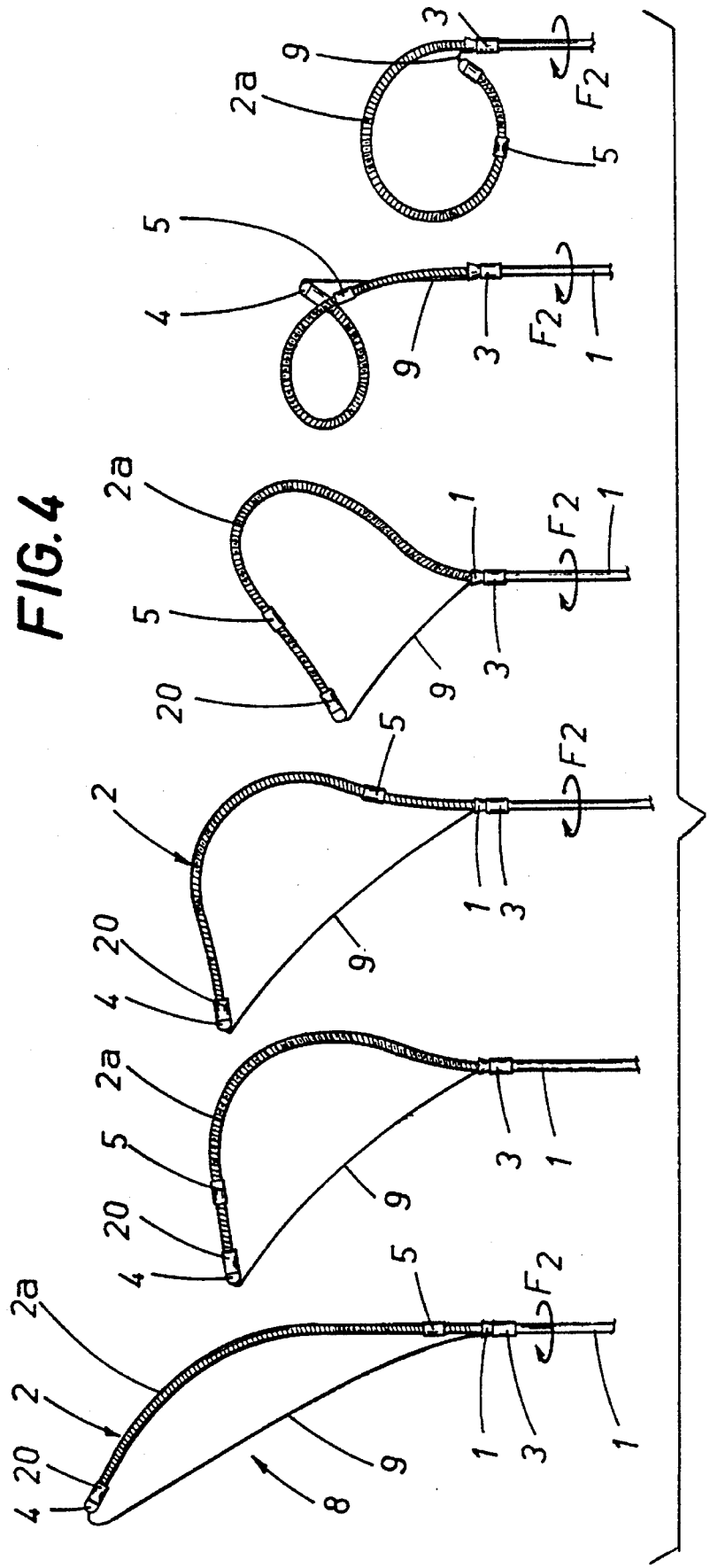
FIG. 4. illustrates certain of the configurations that can be assumed by the operative portion of the electrode catheter of FIGS. 1 to 3, in a series of side elevations.

With reference to the accompanying drawings, the cardiac mapping electrode catheter to which the invention relates is a disposable device, of which the principal elements include: a tubular sheath 1, a first spiral wound wire 2, a medial electrode 5, and means 8 by which to alter the configuration of the first spiral wound wire 2.

More in detail (see FIGS. 1, 2 and 3), the sheath 1 affords a casing for the first wire 2, which is fashioned in a conductive biocompatible material and insulated electrically at least on the surface (for example, by the application of an atomized carbon coating), and insertable intravenously into a cavity of the cardiac muscle (atrium, ventricle or mitral valve). The tubular sheath 1 is encircled by a first ring 3 located near to the distal end, from which the first wire 2 extends into an exposed operative portion 2a terminating at and capped off by a second ring 4. The extremity of the operative portion 2a is fitted over a cylindrical shank 4c afforded by the second ring 4 and held securely in place by a fourth ring 20, positioned over the wire and crimped.

The medial electrode 5, which consists in a sensor embodied in electrically conductive biocompatible material serving to measure the electrical activity of the cardiac muscle, is positioned coaxially to the first wire 2 and capable of movement along the exposed operative portion 2a produced by relative means consisting in a second spiral wound wire 6 disposed coaxially to the first wire 2 and secured at the proximal end to control means 7 operated from outside the body of the patient (such means will be conventional in embodiment, consisting for example in stepping motors controlled by means of a joystick, and therefore are not shown in detail). The geometry of the medial electrode or sensor 5 can be selected to suit the particular anatomical requirements encountered: in FIG. 2 for example, the electrode 5 is illustrated in section (bold lines) as a cylindrical element exhibiting flat external surfaces, and shown in phantom line with spherical external surfaces.

More exactly, the second spiral wound wire 6 (see FIG. 2) is passed slidably and coaxially through the first wire 2 and rigidly associated with a worm 12 rigidly anchored in its turn (by microwelding, for example) to the internal surface of the electrode 5 and coupled helically with the first wire 2 such that a rotation of the second wire 6 left or right will also cause the medial electrode 5 to rotate, and in consequence translate along the operative portion 2a of the first wire 2 in the corresponding direction. The second wire 6 is also accommodated internally of a second sheath 6g and furnished at the distal end with an ogival head 13 of spherical profile seated coaxially in the bore of the distal extremity and positioned at a distance from the electrode 5 such as will afford a certain measure of flexibility and allow the second wire 6 to slide freely through the first wire 2 whenever a change in the configuration of the operative portion 2a is produced by activating the means 8 aforementioned. Such means 8 by which to alter the configuration of the operative portion 2a of the first spiral wound wire 2 are designed to operate between the second ring 4 and the distal end of the first sheath 1, and consist in a flexible tension wire 9 (also of biocompatible material) capable of axial movement in relation to the first wire 2 and establishing a chord, subtended by the operative portion 2a, of which the length can be varied according to the morphology of the cardiac cavity, in such a manner that a rotation of the first spiral wound wire 2 through 360° about its own axis will result in the operative portion 2a engaging in full contact with the entire surface of the cavity. As discernible from FIG. 3, the flexible tension wire 9 is anchored at one end, internally of the second ring 4, by means of a cylindrical retaining element 10 lodged within a cylindrical cavity afforded by the body of the second ring 4; the second ring also presents a domed cap with a through hole 11 affording an exit passage to the wire 9. As illustrated in FIG. 2, the tension wire 9 is taken up through the distal end of the first sheath 1 substantially parallel to the first spiral wound wire 2, stabilized radially and protected by a third spiral wound wire denoted 23 (while obviously retaining freedom of longitudinal movement), and connected by the remaining end to the external control means 7 mentioned previously; thus, the control means 7 can be operated to modify the configuration of the first wire 2 and at the same time to establish a chordal restraint, once the desired configuration is obtained, such as will favor continuous contact of the medial electrode 5 with the walls of the cardiac cavity explored. With the arrangement thus described, whereby the first spiral wound wire 2 and the tension wire 9 are harnessed to the sheath 1 and encircled by the first ring 3 for increased stability, the sheath 1, the first wire 2, the second ring 4 and the tension wire 9 are connected to the control means 7 as a composite assembly and rotatable as one.

For particular medical and technical requirements such as when analyzing the atrial signal, by way of example, the second ring 4 at the free end of the operative portion 2a might be rendered electrically active, likewise the first ring 3 at the end of the sheath 1, if appropriate, in such a way as to equip the catheter with a distal electrode and a proximal electrode; in this instance the electrical signal from the distal electrode 3 can be returned by way of a further conductor 3c as illustrated in FIG. 3. Naturally, the sensing electrode 5 might also be used to effect an ablation of cardiac tissue, in the event that an anomalous electrical activity is detected, by means of a connection to conventional radio frequency appliances (as shown in FIG. 1), or by equipping the catheter with optical fibres and using laser technology.

The manner of utilizing the electrode catheter according to the invention will now be described.

Figure 5:
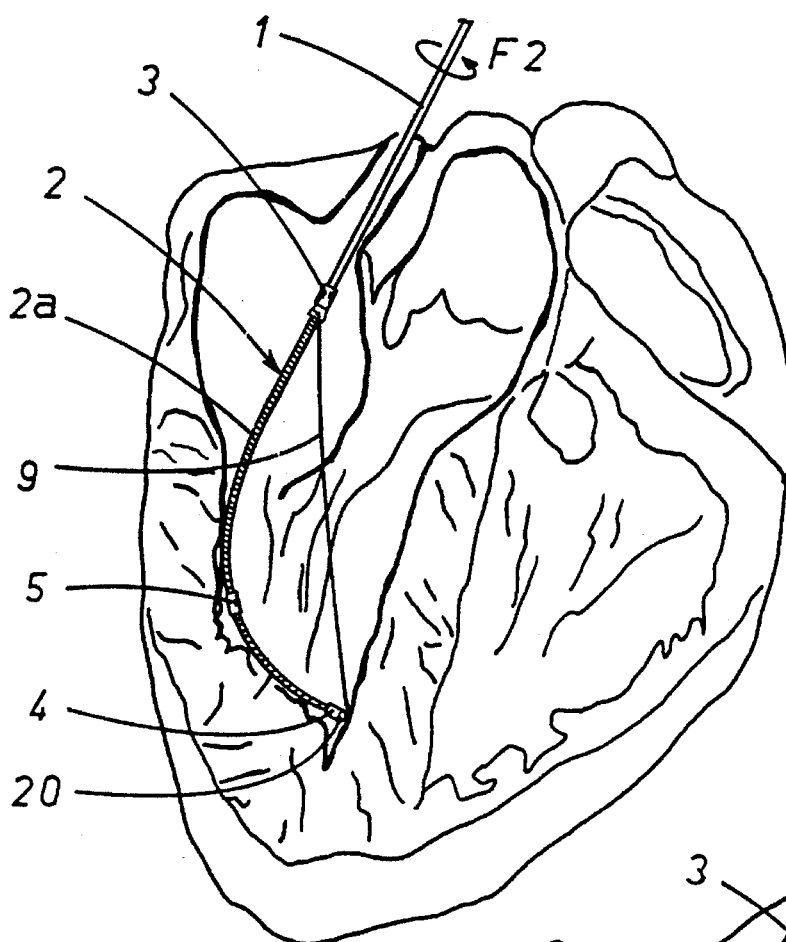
FIGS. 5, 6 and 7 are schematic sectional views of the heart, each showing the electrode catheter in a possible operating configuration inside one of the cardiac cavities.
Figure 6:
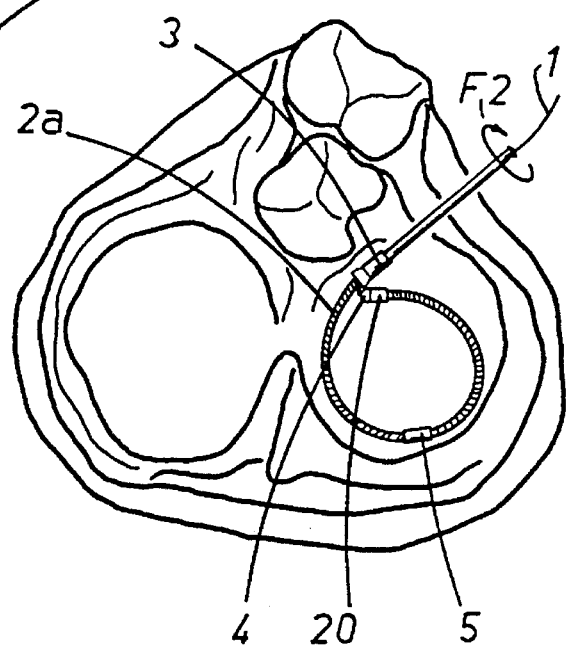
Figure 7:
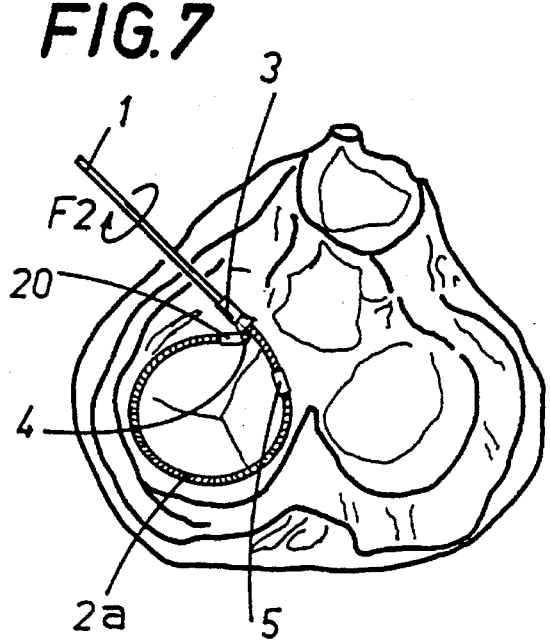

It is the nature of the particular cardiac cavity to be explored that will dictate the selection of the catheter, as regards the diametral dimensions and the size of the exposed operative portion 2a; having made the appropriate selection, the surgeon inserts the catheter through a pulmonary vein and into the myocardium (see FIGS. 1, 4, 5, 6 and 7), then proceeds with the assistance of radioscopic media to initialize the monitoring instruments and the catheter utilizing the proximal and distal electrodes 3 and 4, and if necessary the medial electrode 5 also. This done, the non-active portion of the catheter is secured internally of the vein (by means of conventional technologies represented schematically by the element denoted 30 in FIG. 1), whereupon the surgeon can begin mapping the cardiac cavity under scrutiny, using a control handset 14 to advance or retract the flexible tension wire 9 (see arrow F, FIG. 3) and thereby alter the axial configuration of the operative portion 2a in such a way as to bring the surface of the first spiral wound wire 2, and therefore the medial electrode 5, progressively into contact with the entire band of cardiac muscle that lies adjacent to the operative portion 2a; being offered in contact to the cardiac muscle fibres, in the case of very small cavities in particular, the tension wire 9 functions as a chordal restraint by which the first spiral wound wire 2 is effectively forced into the cavity and kept stably in position throughout the subsequent exploration performed via the medial electrode, or sensor 5. In the examples illustrated, FIG. 1 shows the mapping of the left atrium, FIG. 5 the mapping of the left ventricle, and FIGS. 6 and 7 the mapping of the mitral valve muscle fibres with the heart in diasrole and systole respectively.

As already intimated, the control means 7 allowing manipulation of the first wire 2, tension wire 9 and second wire 6 are incorporated into a single externally operated handset 14, indicated in FIG. 1, which also provides the means by which the catheter is connected up to the electronic and informatic monitoring instruments 21 and 22, also visible in FIG. 1. The control element proper might consist in a joystick 14a, of which the movement will activate a small electric motor keyed to the second spiral wound wire 6 and designed to respond by effecting one full revolution; the flexible tension wire 9 and the means 30 for securing the catheter can be operated by means of a pair of levers 14b.

Once the operative portion 2a is in the required configuration, the surgeon utilizes the handset 14 to rotate the second wire 6 left or right and thus occasion an extending or retracting movement in relation to the first wire 2 (see arrow F1, FIG. 2) such as will alter the position of the electrode 5 and permit of scanning the electrical activity in the zone against which the operative portion 2a of the catheter is brought to bear. Thereafter, still using the handset 14, the securing means 30 can be manipulated to rotate the assembly of the sheath 1, first wire 2, second ring 4 and tension wire 9 through a given angle (arrow F2, FIGS. 5, 6 and 7), while continuing to maintain uniform contact with the endocardium, and thus obtain a full 360° scan of the cardiac cavity; in practice, the surgeon can either rotate the operative portion 2a of the first wire 2 in the cavity with the medial electrode 5 in a fixed position, or produce the selfsame rotation while causing the electrode 5 to translate along the wire 2 at one and the same time.

Clearly, in the event that the exploration should reveal any electrical activity of irregular nature within the cavity, the surgeon can operate without delay utilizing the radio frequency apparatus, the technique being simply to heat the medial electrode and thus allow of "scorching" the muscular tissues that may be at risk or malfunctioning in any way. Several significant advantages are afforded by the electrode catheter described and illustrated: the notable speed with which the catheter is connected and positioned internally of the cardiac cavity to be explored; a practically unlimited anatomical adaptability, thanks to the numerous configurations which can be assumed by the operative portion of the spiral wound wires; precision and completeness in the operation of scanning electrical activity, given the ability of the first wire to rotate 360° while maintaining the selected anatomical profile. It will be noted, moreover, that a probe rotatable through 360° can be employed not only to produce a complete scan of electrical activity but also to effect a measurement of the ring encircling the mitral valve, a procedure difficult to accomplish with previous solutions.

What is claimed is:

1. An intravenous electrode catheter for mapping and operating on cardiac cavities, the catheter comprising:

an elongate tubular outer sheath of biocompatible material, the sheath having a distal end and a proximal end;

a first elongate spiral wound wire of biocompatible and electrically conductive material, received within the tubular sheath and including a distal electrically insulated operative portion extending from the distal end of said sheath;

a first ring disposed at a fixed position on the distal end of the sheath;

a second ring disposed on the distal operative portion of the first elongate spiral wound wire;

a second signal wound wire, disposed coaxially with the first spiral wound wire;

an external operatively associated operator mechanism;

a third ring formed of an electrically conductive and biocompatible material for measuring electrical cardiac activity, the third ring being associated coaxially with the first spiral wound wire and adapted for translatory movement along the operative portion of the first spiral wound wire by means of the second spiral wound wire having at least one end attached to the third ring and remaining end that is not connected to the third ring connected to the external operatively associated operator mechanism for inducing and controlling said translatory movement of the third ring; and altering means for altering a configuration of the operative portion of the first spiral wound wire, said means including a flexible tension element interconnecting the second ring and the distal end of the sheath, the flexible tension element being axially movable in relation to the first wire so as to control the length of the interconnection therebetween according to a cardiac cavity morphology, in such manner that the operative portion can be brought into continuous wiping contact with an interior surface of the cavity by rotating the first spiral wound wire through 360°.

2. The electrode catheter according to claim 1, further comprising a cylindrical retaining element, a domed cap, and a third spiral wirer wherein the altering means includes a flexible tension wire anchored at one end by the cylindrical retaining element lodged within a cylindrical cavity formed in the second ring, the wire passing through a hole in the domed cap forming an integral part of the second ring, the tension wire then being directed along the sheath substantially parallel with the first spiral wound wire and accommodated within the third spiral wound wire, and the tension wire being connected on the remaining end to the external operatively associated operator mechanism.

3. The electrode catheter according to claim 2, further comprising an operator unit connected to the proximal end of the sheath for controlling movement of the first spiral wound wire, of the tension wire and of the second spiral wound wire from outside the body of a cardiac patient.

4. The electrode catheter according to claim 1, wherein
the first spiral wound wire is attached to the tubular sheath and,
the sheath, the first spiral wound wire, the second ring and the tension element are connected as a composite assembly to the external operatively associated operator mechanism in a manner as to allow their collective rotation together as a composite assembly.

5. The electrode catheter according to claim 1, further comprising an electrode movable along the operative portion of the first spiral wound wire, wherein the second spiral wound wire is accommodated slidably and coaxially within the first spiral wound wire, encased in a second sheath and connected to a worm thread rigidly associated with an internal surface of the third ring, the worm thread engaging the first spiral wound wire, such that relative angular movement between the first spiral wound wire and the second spiral wound wire produces translatory movement of an electrode along the operative portion of the first spiral wound wire.

6. The electrode catheter according to claim 5, wherein the second spiral wound wire terminates distally in an ogival head of spherical profile seated coaxially in the distal end of the second wire, the head facilitating sliding movement of the second wire internally of the first spiral wound wire when the relative angular movement between the first spiral wound wire and the second spiral wound wire occurs.

7. The electrode catheter according to claim 1, further comprising a fourth ring crimped over the first spiral wound wire, wherein the operative portion of the first spiral wound wire is fitted over a cylindrical shank defined by the second ring, the shank being secured to the first spiral wound wire by means of the fourth ring crimped over the first spiral wound wire.

8. The electrode catheter according to claim 1, wherein the third ring is substantially cylindrical and includes flat external surfaces.

9. The electrode catheter according to claim 1, wherein the third ring is substantially cylindrical and includes spherical external surfaces.

10. The electrode catheter according to claim 1, wherein the second ring is electrically active to function as a distal electrode.

11. The electrode catheter according to claim 1, wherein the first ring is electrically active to function as a proximal electrode.

12. An electrode catheter comprising:
an elongate body member having a proximal non-active portion and a distal operative portion;
a proximal electrode on a distal end of said non-active portion of the elongate body member;
a distal electrode on a distal end of said operative portion of the elongate body member; and,
a medial electrode axially slidable along the elongate body member in said operative portion between said distal electrode and said proximal electrode.

13. The electrode catheter according to claim 12 further comprising a translating member for effecting axial slidable motion of said medial electrode in said operative portion between said distal electrode and said proximal electrode.

14. The electrode catheter according to claim 13 further comprising an external motion control device, wherein said translating member includes a first elongate member passing through said non-active portion of the elongate body member and connecting the medial electrode to the operatively associated external motion control device.

15. The electrode catheter according to claim 14 wherein:
the first elongate member is a flexibly resilient helical member; and,
the medial electrode threadedly engages the flexibly resilient helical member.

16. The electrode catheter according to claim 15 further comprising a second elongate member connecting said medial electrode to said operatively associated external motion control device for preventing axial rotation of the medial electrode while the first elongate member is axially rotated.

17. The electrode catheter according to claim 16 further wherein said second elongate member is an electrically conductive for electrically connecting the medial electrode to an operatively associated external electric device.

18. The electrode catheter according to claim 17 wherein said first elongate member is electrically conductive for connecting said distal electrode to said operatively associated external electric device.

19. The electrode catheter according to claim 12 further comprising a translating member for effecting axial rotation of said medial electrode in said operative portion.

20. The electrode catheter according to claim 19 further comprising an external motion control device, wherein said translating member includes a first elongate member passing through said non-active portion of the elongate body member and connecting said medial electrode with the operatively associated external motion control device.

21. The electrode catheter according to claim 20 wherein said first elongate member is an electrically conductive member for electrically connecting the medial electrode to an operatively associated external electrode device.

22. The electrode catheter according to claim 12 further comprising a translating member for effecting i) axial slidable motion of said medial electrode in said operative portion between said distal electrode and said proximal electrode, and ii) axial rotation of said medial electrode in said operative portion.

23. The electrode catheter according to claim 22 further comprising an external motion control device., and wherein said translating member includes:
a first flexibly resilient helical member threadedly engaged with said medial electrode and passing through said nonactive portion of the elongate body member for connecting the medial electrode to the operatively associated external motion control device; and,
a second member connecting said medial electrode to said operatively associated external motion control device for preventing axial rotation of the medial electrode while the first elongate member is axially rotated.

24. The electrode catheter according to claim 23 wherein said first ember is an electrically conductive member for electrically connecting the distal electrode with an operatively associated external electric device; and, said second member is an electrically conductive member for electrically connecting the medial electrode to said operatively associated external electric device.

25. The electrode catheter according to claim 12 further comprising an altering member for altering an axial configuration of the distal operative portion of said elongate body member.

26. The electrode catheter according to claim 25 further comprising an external motion control device, and wherein said altering member is a flexible tether connecting a distal tip of said distal electrode to the operatively associated external motion control device, the Eelher extending through said non-active portion of the elongate body member and exiting said distal end of said non-active portion to pass outside said operative portion.

27. An electrode catheter comprising:

an elongate body member having a longitudinal axis and defining a proximal non-active portion and a distal operative portion; and, a first electrode having an internal helical surface for engaging the elongate body member, said first electrode being axially slidable along the elongate body member in said operative portion.

28. The electrode catheter according to claim 27 further comprising an external motion control device, and a translating member for effecting axial slidable motion of said first electrode in response to the operatively associated external motion control device.

29. The electrode catheter according to claim 27 further comprising an external motion control device, a medial electrode, and a translating member for effecting axial rotation of said medial electrode in response to the operatively associated external motion control device.

30. The electrode catheter according to claim 27 further comprising an external motion control device, a medial electrode, and a translating member for effecting i) axial slidable motion of said medial electrode, and ii) axial rotation of said medial electrode, in response to the operatively associated external motion control device.

31. The electrode catheter according to claim 27 further comprising an altering member for altering an axial configuration of the distal operative portion of said elongate body member.

* * * * *